(12) United States Patent
Wintsch et al.

(10) Patent No.: US 10,893,932 B2
(45) Date of Patent: *Jan. 19, 2021

(54) IMPLANT AND METHOD FOR PRODUCING THE SAME

(71) Applicant: BIOTRONIK AG, Buelach (CH)

(72) Inventors: Daniel Wintsch, Zurich (CH); Stefan Loher, Zurich (CH); Bodo Quint, Dettighofen (DE); Patrice Bachmann, Winterthur (CH); Hans Lang, Buchs (CH); Dragica Pantic, Zurich (CH); Alwin Schwitzer, Buelach (CH)

(73) Assignee: BIOTRONIK AG, Buelach (CH)

( * ) Notice: Subject to any disclaimer, the term of this patent is extended or adjusted under 35 U.S.C. 154(b) by 21 days.

This patent is subject to a terminal disclaimer.

(21) Appl. No.: 16/358,543

(22) Filed: Mar. 19, 2019

(65) Prior Publication Data

US 2019/0314137 A1    Oct. 17, 2019

Related U.S. Application Data

(63) Continuation of application No. 13/090,479, filed on Apr. 20, 2011, now Pat. No. 10,271,941.

(Continued)

(51) Int. Cl.
*A61F 2/07* (2013.01)
*A61L 31/06* (2006.01)
*A61F 2/90* (2013.01)

(52) U.S. Cl.
CPC ............... *A61F 2/07* (2013.01); *A61L 31/06* (2013.01); *A61F 2/90* (2013.01);

(Continued)

(58) Field of Classification Search
CPC ..................... A61F 2/82; A61F 2/07
See application file for complete search history.

(56) References Cited

U.S. PATENT DOCUMENTS

| 6,325,823 B1 | 12/2001 | Horzewski et al. |
| 2004/0267362 A1 | 12/2004 | Hwang et al. |
| 2011/0262684 A1 | 10/2011 | Wintsch et al. |

FOREIGN PATENT DOCUMENTS

| DE | 2654658 A1 | 6/1977 |
| EP | 1493404 A1 | 1/2005 |

(Continued)

OTHER PUBLICATIONS

EP11160805 European Search Report dated Aug. 19, 2013.
EP18207291 European Search Report dated Mar. 6, 2019.

*Primary Examiner* — Matthew W Schall
(74) *Attorney, Agent, or Firm* — Wagenknecht IP Law Group, PC (57) ABSTRACT

An implant having a preferably hollow cylindrical basic structure. A nonwoven fabric is disposed in and/or on the basic structure, the nonwoven fabric preferably comprising biocompatible thermoplastic polyurethane and/or a polymer selected from the group consisting of polylactic acid, polycaprolactone, and a copolymer thereof, and/or a polymer including polyphosphazene. At least in at least one section of the implant, preferably at the proximal and/or distal ends of the implant, fastening means are provided or the nonwoven fabric is treated such that, at least in the expanded state of the implant, the protrusion of nonwoven fabric sections from the implant is significantly reduced. Furthermore, a method for producing such an implant is provided.

9 Claims, 8 Drawing Sheets

Related U.S. Application Data

(60) Provisional application No. 61/327,113, filed on Apr. 23, 2010.

(52) U.S. Cl.
CPC . *A61F 2002/072* (2013.01); *A61F 2250/0063* (2013.01); *Y10T 428/24008* (2015.01)

(56) References Cited

FOREIGN PATENT DOCUMENTS

| | | | |
|---|---|---|---|
| WO | 9308767 | A1 | 5/1993 |
| WO | 9724081 | A1 | 7/1997 |
| WO | 03087443 | A1 | 10/2003 |
| WO | 2006065665 | A1 | 6/2006 |

# IMPLANT AND METHOD FOR PRODUCING THE SAME

CROSS REFERENCE TO RELATED APPLICATIONS

This is a continuation of U.S. patent application Ser. No. 13/090,479, filed Apr. 20, 2011, which claims benefit of priority to U.S. patent application Ser. No. 61/327,113, filed Apr. 23, 2010; the contents of which are herein incorporated by reference in their entirety.

TECHNICAL FIELD

The present invention relates to an implant, particularly an intraluminal endoprosthesis, having a preferably hollow-cylindrical basic structure, and to a method for producing such an implant.

BACKGROUND

Medical endoprosthesis or implants for a wide variety of applications are known from the state of the art in great diversity. Implants as defined by the present invention shall be endovascular prostheses or other endoprostheses, such as stents (vascular stent, bile duct stent, mitral stent), endoprostheses for closing patent foramen ovale (PFO), pulmonary valve stent, endoprosthesis for closing an atrial septal defect (ASD), prosthesis in the area of hard and soft tissue, and also anchoring elements for electrodes, in particular pacemakers or defibrillators.

These days, stents that are used for the treatment of stenoses (vascular constrictions) are employed especially frequently as implants. They have a body in the shape of an optionally perforated tubular or hollow-cylindrical basic structure, which is open at both longitudinal ends. The basic structure of the stent can be composed of individual mesh sections, which are formed by zigzag- or meander-shaped struts. The tubular basic structure of such an endoprosthesis is inserted into the vessel requiring treatment and is intended to support the vessel. Stents have become established especially for the treatment of vascular diseases. Constricted areas in the vessels can be expanded through the use of stents, resulting in increased lumen. While through the use of stents or other implants, an optimal vessel cross-section can be achieved, which is primarily necessary for a successful therapy, however the lasting presence of such a foreign object triggers a cascade of microbiological processes, which favor inflammation of the vessel to be treated or necrotic vascular changes, for example, and due to the formation of plaque may result in gradual blockage of the stent.

Stent grafts refer to stents which on or in their frequently lattice-shaped basic structure also contain a nonwoven fabric, or another planar covering, such as a film. Here, a nonwoven fabric shall be understood as a textile surface structure which is formed by individual fibers. The term nonwoven fabric in the present invention also includes the case where the textile surface structure is made of only a single "endless" fiber. Such a stent graft is used, for example, to reinforce weak spots in arteries, such as in the region of an aneurysm, or a rupture in the vessel wall (bail-out device), in particular as an emergency stent.

Known stents, which are provided with a PTFE film or an ePTFE film, exhibit poor ingrowth behavior in the vascular system due to the film structure. In a variant of a stent graft known from the prior art, for example, an ePTFE film is disposed in a sandwich-like manner between two stent lattice structures. It has been shown that such a stent graft is very rigid, so that it has an increase restenosis rate due to the increased flexural strength of the sandwich structure. The ePTFE film structure has worse endothelialization and poorer transmural communication. Furthermore, such a "sandwich" stent graft is difficult or impossible to apply to the desired lesion, particularly in the case of tortuous vessel anatomy.

The published prior art WO 03/087443 A1 describes a fiber-like covering for a stent, which is applied onto the supporting structure by way of electrospinning. In this published prior art, the fiber materials used are PET, PLA, PGA, or PCL. Although the stent grafts produced from these materials have comparatively high porosity, so that in critical regions the flow in the capillaries of the wall of the vessel being treated is ensured, and therefore good endothelialization can be achieved, an increase rate of complications was observed with such an electrospun stent graft.

From the document CA 2 567 954 A1, a stent graft is known, in which better bonding of the graft material to the respective strut is to be achieved by suturing the graft material in the region of the struts and/or by using a washer on a strut. Yet, the rate of complications was not reduced by fixing the graft material in this manner.

SUMMARY

It is therefore the object of the present invention to create an implant which has a lower rate of complications and continued good endothelialization. Furthermore, a method for producing such an implant is provided.

The above object is achieved by an implant having a basic structure, and a nonwoven fabric disposed in and/or on the basic structure, wherein in at least one section of the implant, preferably at the proximal and/or distal ends of the implant, a fastening means preferably acting over a large area is provided or the nonwoven fabric on the basic structure is treated such that, at least in an expanded state of the implant, a protrusion of nonwoven fabric sections (flaps) from the basic structure and/or the formation of more extensive regions from which fibers or fiber sections protrude from the basic structure is significantly prevented or reduced.

In some embodiments, the fastening means includes a torsion spring disposed on the inside of the basic structure and/or on the outside of the basic structure. The fastening means can be strut elements, such as those that extend in the axial direction; a hydrogel and/or a hydrogel-based adhesive, which is disposed on an outside of the nonwoven fabric; axially extending reinforcement elements, which are provided on the basic structure; or an elastic element, such as an elastic ring. Further, the fastening means may be formed in the at least one section by connectors disposed on the basic structure.

In some embodiments, the nonwoven fabric is produced by way of electrospinning and in some embodiments, is treated to increase its thickness.

In another aspect of the invention a method for producing an implant, such as an implant having a hollow cylindrical basic structure is provided. The method includes providing a basic structure; disposing at least a first part of a nonwoven fabric on and/or in the basic structure, optionally by way of electrospinning; and introducing and/or applying a fastening means and/or treating the nonwoven fabric in at least one section, optionally at proximal and/or distal ends of the implant, such that, at least in an expanded state of the implant, protrusion of nonwoven fabric sections or fibers from the basic structure is prevented or reduced. In some embodiments the method further includes disposing a second part of a nonwoven fabric on and/or in the basic structure, such as by way of electrospinning; and still further embodiments include fastening the implant on a catheter, such as on a balloon of the catheter.

In some embodiments the nonwoven fabric is compacted at least in the at least one section by a method selected from the group consisting of a laser method, a thermal method, a solvent application, a solvent vapor application, and a combination thereof. Further, the nonwoven fabric can be compacted to produce an elastic element, optionally an elastic ring, in the at least one section. In some embodiments, a hydrogel and/or a hydrogel-based adhesive is disposed on the outside of the nonwoven fabric.

The method may also include inserting at least one torsion spring in the at least one section on an inside of the implant and/or at least one torsion spring on the outside. In some embodiments, the nonwoven fabric is perforated by laser in the at least one section.

To the credit of the inventors, they discovered that with respect to stents formed in part from nonwoven fabric, without using any additional, in particular extensive fastening measures, that is, also such acting between the mesh, flaps of nonwoven fabric will form on the stent graft. Specifically, formation was found to occur by tensioning the stent during expansion or dilation. These flaps or more extensive regions having protruding fibers or fiber sections, which can be created in particular at the distal or proximal end of the stent, are pulled into the treated vessel as a result of the pressure developing from the flow rate of the body fluid, thereby preventing flow of the body fluid, such as blood, through the treated vessel. Such a process creates an increased risk of thrombosis.

Even if no flaps are observed on a stent graft, frequently loose fiber sections of the filaments or loose individual fibers may occur at the surfaces in more extensive regions and likewise impair the flow of body fluid.

For this reason, according to the invention, in one section or in several sections of the implant, which is or which are particularly susceptible to an increased risk of thrombosis, preferably at the proximal and/or distal ends of the implant, the nonwoven fabric is connected to the basic structure or treated such that the nonwoven fabric, loose fibers or fiber sections cannot detach from the basic structure, in particular when feeding, positioning and releasing the implant and during the intended duration of function. As a result, complications are prevented. In addition, the restenosis rate is reduced due to improved hemodynamics, particularly if the section is located at the proximal or distal end of the implant.

A significant reduction in the protrusion of nonwoven fabric sections or more extensive regions of fibers as used herein, refers to fiber sections having a protruding length of generally within a fraction of a millimeter from the section of the implant. When nonwoven fabric is treated or when the implant is provided with a fastening means, significant reduction can be achieved, in which at least 90% fewer, and more preferably no fibers, fiber sections or nonwoven fabric sections protrude from the implant. The average distance of the protruding fibers, fiber sections or nonwoven fabric sections of the end or region thereof which protrudes the furthest and with which they protrude into the lumen of the treated vessel is significantly reduced by the basic structure, preferably by at least 90%, and more preferably completely, compared to the state without treatment or fastening means.

The technical approach taken by the present invention significantly differs from that described in CA 2 567 954 A1 ("the '954 Applications") in that while the technical approach taken in the '954 Applications can prevent such flaps by suturing, it cannot prevent the protrusion of more extensive loose fiber sections or loose fibers because the approach only acts in the region of the struts of the basic structure. Additionally, the method is very complex and susceptible to error.

The solution according to the invention has the advantage that the nonwoven fabric has a certain level of elasticity which prevents tearing of the nonwoven fabric, particularly when dilating the stent graft, in particular if it comprises a thermoplastic elastomer (TPE). Particularly preferred is a thermoplastic polyurethane and/or a biodegradable polymer. Preferably a polymer is selected from the group or family of polylactic acid or polycaprolactone, or copolymers thereof (such as PCL/TMC), and/or a biocompatible, inorganic polymer, preferably from the group or family of polyphosphazenes. At the same time, the recoil of the implant is not negatively influenced by the additional nonwoven fabric casing, compared to the basic structure having no nonwoven fabric.

Due to the use of nonwoven fabric, the porosity of the implant can also still be specifically influenced, so that transmural communication is enabled in critical regions.

Such implants can be used, for example, as a bail-out stent, neurostent, drug eluting stent, graft on balloon (PEB), percutaneous transluminal angioplasty (PTA), as arterial or vein replacement, or anchoring elements for pacemaker or defibrillator electrodes.

In a preferred embodiment, the fastening means is formed by a torsion spring which is disposed proximally and distally on the inside of the basic structure, or on the outside of the basic structure. Such a torsion spring is preferably designed as a compression spring, which is inserted in the interior of the implant, in the case of a hollow cylindrical implant, and pressed against the inside wall of the implant. The torsion spring preferably comprises surface elements which have the shape of a hollow cylindrical section and which, even in the expanded state of the implant, cover the inner or the outer surface of the implant such that fibers, fiber sections or nonwoven fabric sections cannot protrude from the basic structure into the inside of the implant. It is also possible to dispose a plurality of such torsion springs on the inside of the basic structure and/or outside on the basic structure.

Such a torsion spring is preferably made of the same material as the basic structure, it being particularly preferred if it is produced simultaneously with the production of the basic structure without any additional fastening steps. Such a torsion spring preferably has a modulus of elasticity of approximately 30 GPa to approximately 230 GPa.

In a further embodiment, flaps are prevented in that the basic structure in the at least one section of the implant has connectors extending substantially in the circumferential direction and serving as fastening means. The advantage of such additional connectors is that the nonwoven fabric is supported in the respective section by the basic structure and the connector, thereby preventing flaps. These connectors, like the torsion spring described above, can be produced from the same material as the basic structure. In the at least one section, these connectors are present in addition to the elements (struts) of the basic structure, which optionally may also extend in the circumferential direction. Such connectors preferably have a structure and/or shape that is adapted to the function thereof. These connectors, for example, can have a wall thickness which is reduced by at least 50% compared to the struts, preferably a wall thickness which is reduced by at least 70% compared to the struts.

These thin-walled connectors are very flexible, so that a plurality of connectors can be installed in the stent structure without impairing the stent during opening. In addition, when mounting the stent graft on the balloon, a profile having a low height can be implemented with such connectors, due to the low wall thickness thereof.

In a further preferred embodiment, the fastening means is formed by additional, particularly substantially axially extending strut elements, which are disposed in the particular section in addition to the basic structure. Due to the increased number of axial supports for the basic structure in the at least one section of the implant, the mechanical fixation of the nonwoven fabric to the vessel wall (which is modified in the section) after dilation is improved. As a result, a detaching of the nonwoven fabric from the basic structure is less critical and the risk of thrombosis due to flaps is reduced. In a particularly preferred embodiment, these axially extending strut elements reduce a mesh length in the circumferential direction by half.

It is furthermore preferred if the fastening means is formed by a coating, which is provided at least in some regions and which is disposed on the outside of the nonwoven fabric and comprises a material that forms a hydrogel and/or a hydrogel-based adhesive. This means that the coating in the at least one section of the implant, in which the fastening means is disposed, covers at least part of the outer lateral area of the nonwoven fabric. The coating may also cover the entire lateral area of the nonwoven fabric in the particular section of the implant.

The advantage of this embodiment is that the material with the hydrogel swells due to water absorption from the body fluid, so that an attractive interaction takes place between the outer surface of the implant (that is, the outer surface of the nonwoven fabric) and the vessel wall. In this way, the implant is virtually glued to the vessel wall. This measure can prevent the formation of flaps, because the nonwoven fabric is fixed to the vessel wall, and can reduce the risk of thrombosis. The material preferably comprises one or more compounds of the group consisting of polyethyleneoxide, polyvinylpyrrolidone, polyvinyl alcohol, polyacrylate, agarose, methylcellulose, polyaspartic acid, polyhyaluronic acid, pullulan, polysaccharides, in particular dextran. It is also conceivable that this hydrogel forms a bond with a pharmaceutically active substance, such as heparin or heparansulfate, or facilitates the embedding of such a substance. In this way, an additional function of the coating is implemented.

A pharmaceutically active substance (or therapeutically active or effective substance) shall be a plant, animal or synthetic active ingredient (drug) or a hormone, which in a suitable dose is used as a therapeutic agent for influencing states or functions of the body, for substituting active ingredients produced naturally by the human or animal body, such as insulin, and for eliminating, or rendering harmless, pathogens, tumors, cancer cells or substances foreign to the body. The release of the substance in the surroundings of the endoprosthesis has a positive effect on the healing process or counteracts pathological changes of the tissue as a result of the surgical procedure, or in oncology is used to render diseased cells harmless.

Such pharmaceutically active substances, for example, have an anti-inflammatory and/or antiproliferative and/or spasmolytic effect, whereby, for example, restenoses, inflammations or (vascular) spasms can be avoided. In particularly preferred embodiments, such substances may comprise one or more substances of the active substances groups consisting of the calcium channel blockers, lipid regulators (such as fibrates), immunosuppressants, calcineurin inhibitors (such as tactrolimus), antiphlogistics (such as cortisone or dichlofenac), anti-inflammatory agents (such as imidazoles), anti-allergic drugs, oligonucleotides (such as dODN), estrogens (such as genistein), endothelial forming agents (such as fibrin), steroids, proteins, hormones, insulins, cytostatic drugs, peptides, vasodilators (such as sartanes), and the antiproliferatively acting substances of the taxols or taxanes, preferably paclitaxel or sirolimus.

A material with hydrogel is applied, for example, from a solution (such as 5-20% by weight of the polymer in the solution) with a solvent that is suitable for the polymers forming the hydrogel (such as specially dried chloroform, DMF, THF) in the presence of a cross-linking agent (such as hexamethylene diisocyanate or the more suitable butane diisocyanate) as a reactive mixture to the outside of the nonwoven fabric and dried. Due to an additive reaction of the isocyanate and cross-linking resulting in part therefrom, a closed hydrogel-forming coating is formed, which has a layer thickness of approximately 10 µm to approximately 20 µm. Upon contact with water, a hydrogel forms on the outside of the implant, which has an attractive interaction with the vessel wall and fixes the nonwoven fabric of the implant to the vessel wall. As a result, flap formation is prevented, and the risk of thrombosis due to the implant is reduced or prevented. Another advantage of a hydrogel coating is that it can positively influence the biocompatibility of the membrane. For example, when using hydrogels that are based on polyethylene glycol, the foreign-body reaction can be suppressed sufficiently so that nearly no reaction can be detected.

It is furthermore advantageous if the fastening means is formed by preferably axially extending reinforcement elements, with which the basic structure is provided in the particular section. The advantage of these reinforcement elements is that the nonwoven fabric is fastened better, thereby preventing flaps and lowering the risk of thrombosis. Compared to the incorporation of additional struts into the basic structure, this embodiment has the added benefit that the struts can be fastened subsequently to any arbitrary location of the basic structure. In this way, the implant can be optimally adapted to the particular requirements during treatment.

The reinforcement elements preferably comprise at least one metal and/or a material that has a high modulus of elasticity, and/or a material that has at least significantly higher rigidity than the polymer forming the nonwoven fabric. In principle, metallic and polymeric biodegradable biocompatible materials are likewise suited. In a preferred embodiment of a production method for an implant having reinforcement elements, the basic structure is first coated with a very thin nonwoven layer using a spinning process. The reinforcement elements are then placed onto the nonwoven layer and fixed in place. This can be implemented, for example, in that the reinforcement elements are first wetted with a polymer solution that is similar to the spinning solution. Thereafter, the individual reinforcement elements are appropriately positioned on the coated basic structure in the uncured state of the wetting layer, whereupon the reinforcement elements are instantly glued to the coating. After the elements have been placed, another nonwoven layer is spun on the composite body. In a subsequent compacting process (described below), a closed material composite is produced. The axial reinforcement elements reduce the risk of flap formation. The length of such a reinforcement element is preferably 1 mm to several millimeters, the width and height are preferably less than 0.5 mm, with less than 0.1 mm being particularly preferred. The reinforcement elements preferably produce a flat cuboid shape. The reinforcement elements can be made of 316L stainless steel, for example, having a height of less than 0.05 mm, a width of approximately 0.1 mm, and a length of approximately 2 mm.

In order to tension the nonwoven fabric, in a preferred embodiment an elastic element may be provided as the fastening means, preferably an elastic ring. Such an elastic element is preferably produced from the nonwoven fabric in a subsequent treatment step. It is therefore rigidly connected to the nonwoven fabric in the particular section. The modulus of elasticity of such an elastic element is preferably approximately 10 MPa to approximately 40 Mpa, and the maximum elongation is preferably greater than 300%.

The nonwoven fabric is preferably produced by way of electrospinning. During electrospinning, a polymer solution, preferably a solution comprising a nonwoven polymer as listed above, is delivered through a metal nozzle. Between the metal nozzle and the basic structure, a high voltage is applied. The basic structure has a different potential than the metal nozzle. By feeding the polymer solution and due to the voltage difference between the nozzle and the basic structure, a filament is applied onto the basic structure as a nonwoven fabric.

It is furthermore advantageous if the nonwoven fabric in the at least one section is treated such that it has a higher density, that is, it is compacted. A higher density of the nonwoven fabric can be achieved, for example, by mechanical treatment, thermal treatment, and/or by treatment with a solvent and/or solvent vapor. Such a treatment, which hereinafter is also referred to as a compacting process, reduces the likelihood of fibers or fiber sections detaching or protruding from the nonwoven fabric. In addition, compacting increases the compressive strength of the nonwoven fabric and influences porosity.

The basic structure of such an implant can preferably comprise a metal or a metal alloy, preferably stainless steel, CoCr, a magnesium alloy (implant designed as a stent comprising a magnesium alloy is also referred to as AMS=absorbable metal stent), and/or nitinol, and/or a polymer from the category of biodegradable polymers, preferably polylactic acids, polycaprolactone, and/or mixtures of copolymers thereof, and/or a polymer from the category of biocompatible polymers, preferably UHMWPE and/or PEEK. In a further embodiment, a metallic basic structure can additionally be provided with a coating made of amorphous silicon carbide (aSiC coating).

The above object is also achieved by a method for producing an implant, comprising the following steps:
  providing a basic structure;
  disposing at least a first part of a nonwoven fabric on and/or in the basic structure, preferably by way of electrospinning; and
  introducing and/or applying a fastening means and/or treating the nonwoven fabric in at least one section, preferably at the proximal and/or distal ends of the implant, such that, at least in an expanded state of the implant, the protrusion of nonwoven fabric sections from the basic structure and/or the formation of more extensive regions in which fibers or fiber sections protrude from the basic structure, are significantly reduced;
  optionally disposing a second part of a nonwoven fabric on and/or in the basic structure, preferably by way of electrospinning;
  optionally fastening the implant on a catheter, preferably on a balloon of the catheter.

Such a method is a simple way to produce an implant, which is endothelialized well due to the porosity thereof. In addition, the implant poses a reduced risk of thrombosis, because, when the nonwoven fabric is produced by way of the method according to the invention, parts of the nonwoven fabric (fibers or fiber sections) are prevented from protruding into the lumen into which the body fluid flows.

In particular when the fastening means, preferably an axially extending reinforcement element as described above, is to be embedded into the nonwoven fabric, it is advantageous if first a first part of the nonwoven fabric is disposed on the basic structure, then the fastening means is disposed in a section of the implant and/or in the nonwoven fabric, and thereafter a second part of the nonwoven fabric is disposed on the basic structure, which has been provided with the first part of the nonwoven fabric and the fastening means.

In an alternative embodiment, however, it is also possible to dispose the entire nonwoven fabric material first on the basic structure and to then introduce and/or apply the fastening means and/or treat the nonwoven fabric.

The porosity of the nonwoven fabric, and consequently also the endothelialization and/or blood permeability and the compressive strength of the nonwoven fabric, can be controlled by the parameters of the electrospinning process and by the parameters of the compacting process. Due to the elasticity of the nonwoven fabric, the rigidity of the basic structure is changed only insignificantly, which results neither in any additional contribution to the recoil of the basic structure, nor in an increased restenosis rate due to increased rigidity.

In a particularly preferred embodiment, the nonwoven fabric is compacted in at least one section by thermal treatment, mechanical treatment and/or by interaction with at least one solvent, a dispersion and/or an adhesive solution. Compacting as used hereinafter shall refer to a measure by which a nonwoven fabric is intensively cross-linked and fixed. In the at least one section, the nonwoven fabric is cross-linked more strongly than in the remaining sections in which no compacting took place.

Optionally, the implant is severed at a predetermined location after compacting, thereby ensuring, for example, a certain length of the implant. Furthermore, preferably in connection with the severing of the implant at a predetermined location, compacting can be carried out so intensively that an elastic element is produced. Below, a few exemplary embodiments are described as to how compacting can be achieved, or how compacting can be carried out so intensively that an elastic element is obtained.

A preferred thermal treatment for compacting the nonwoven fabric includes a heating step, or several heating steps, such as in a circulating air oven, which cause the fibers of the nonwoven fabric to be sintered together in the particular section by selecting a temperature below that at which polymer softens and selecting a suitable time period. By mounting an implant that is provided with the nonwoven fabric beneath a heat-shrinkable tube, a smooth and homogeneous surface structure of the nonwoven fabric can be achieved after completing the thermal treatment, which mechanically compresses the fiber structure due to the shrinkage process.

A particularly preferred and very productive variant of compacting by thermal treatment is carried out by way of electromagnetic radiation. When using electromagnetic radiation, the fibers of the nonwoven fabric can be heated very briefly by way of the self-absorption thereof. The wavelengths of the available radiation are very important, because by way of absorption and scattering inside the fiber, they determine the penetration depth into the fibers. In the above nonwoven polymer types, monochromatic laser radiation in the NIR produces only low absorption and a high penetration depth, and consequently homogeneous thermal compaction of the fiber structure.

A further technically interesting embodiment is attained by uncolored additives, such as CLEARWELD (Gentex Corp, USA), which as additives to the fiber material of the nonwoven fabric, or as coatings on the nonwoven fabric, allow the use of inexpensive and powerful solid matter or diode lasers in the wavelength range of 1100 nm to approximately 750 nm as a radiation source for compacting. The significantly longer-wave radiation of a $CO_2$ laser and the frequently very high self-absorption of the above polymers produces compacting of the irradiated surface a few µm thick. This compacting due to the energy absorption from radiation is produced by the thermal heating of the radiation absorption. In this way, for example, an electrospun nonwoven fabric layer made of Pellethane can be provided with a surface that is made of a very thin, nonmolten and dense polymer layer covering the nonwoven-like substructure using $CO_2$ laser radiation. In this embodiment, suitable parameter selection serves only the melting of the spun polymer fibers on the surface of the nonwoven fabric.

Compacting by way of electromagnetic radiation is above all advantageous for configuring a boundary layer on the outside of the nonwoven fabric that is more stable under mechanical load. For example, the outer nonwoven fabric of the coated basic structure, in particular in the case of a stent that is mounted on the catheter, can be protected better against mechanical loads, such as passing through a hemostatic sheath. Furthermore, better gripping for handling during the treatment with the implant or during the production process can be achieved. In general, the high application of energy in the surface is suited well to melt protruding structures and fix them to the nonwoven fabric surface. These advantages are achieved in that, surprisingly, the fibers protruding from the nonwoven fabric, which are preferably melted, are considerably shortened during softening and therefore very effectively connected to other fibers disposed on the surface of the nonwoven fabric by way of a melting process.

A further variant of compacting is the interaction with solvents. Swelling of the nonwoven polymer is achieved by very potent solvents, such as the effect of THF on different polyurethanes, or chloroform on lactic acid-based absorbable polymers. However, this process is interrupted before the polymer is completely dissolved. This swelling can take place by the absorption of the solvent from the gas phase (compacting by way of solvent vapor) or by direct contact with the solvent. When the swelling agent or solvent is absorbed through the gas phase, the saturation vapor pressure of the swelling agent that is employed can be adjusted by mixing it with other solvents. In the case of direct contact with the solvent, the swelling can additionally be controlled by adding non-solvents. For many polyurethanes as the nonwoven material, for example, such a system is a mixture of THF and water.

During compacting by way of solvents, a considerable relaxation of the spun fibers of the nonwoven fabric can be observed. This relaxation causes tension to build in the planar design of the fiber structure, the structure contracts increasingly and is thereby mechanically compacted. Visually, this process is apparent in that typically the fibers of the nonwoven fabric nestle against the spun basic structure after the spinning process. After the compacting process, a membrane-like fiber structure is spanned between the appropriate elements of the basic structure and delaminates from the basic structure in the edge regions of the basic structure. This process produces a higher number of contact points in the fiber structure, which is still loose after spinning. It can also be observed that fiber structures which may still protrude slightly nestle against the surface.

Other solvents or solvent mixtures comprise tetrahydrofurane (THF) or dimethylformamide (DMF), or a mixture of these solvents (individually or in combination with water or simple alcohols (methanol, ethanol, isopropanol)).

The compacting processes described prevent parts of the nonwoven fabric from protruding from the basic structure. Since the spinning process produces the fiber structure potentially from a continuous fiber, and since the compacting method results in multiple fixation points of the fiber at the connecting points, it is ensured that the mechanically intact planar fiber structure (nonwoven fabric) can give off no fiber fragments whatsoever to the surrounding area.

In order to compact and cut the implant, the implant, which has already been provided with the nonwoven fabric, is mounted, for example on a mandrel, which is connected to a rotating motor. Thereafter, the proximal and/or distal ends of the implant are severed by way of mechanical shearing, such as by way of a rotating blade.

An interesting variant of the method is the use of a focused laser beam for the purpose of severing or for perforating the nonwoven fabric. As described for the compacting process, the spun and oriented fibers are subject to strong relaxation prior to melting. This effect can be utilized in order to achieve axial melting of the fiber material and effective radial retraction of this melt, while rotating the implant provided with the nonwoven fabric and locally axially heating the fiber material by a focused laser beam.

As was already described above, the compacting and/or severing can be done so intensively that an elastic element, preferably an elastic ring, is formed by the nonwoven fabric in the particular section, which likewise prevents the protrusion of fibers or fiber segments in the particular region.

In the above-described severing of the nonwoven fabric by way of a laser beam, particularly during experiments with spun PUR fibers, it was found that, depending on the laser parameters, the relaxation of the nonwoven fiber(s) is so strong that the melt separates. A particular property of this separating point is that the molten fiber ends produce a radial accumulation of polymer, which then solidifies in a disoriented state. This behavior applies in principle to all heat processable polymers, not only to TPU (thermoplastic polyurethane). Due to the width of the laser beam and the small displacement thereof in the axial direction, molten material is accumulated at the fusion line. If the fusion line of the nonwoven fabric reaches the basic structure of the implant, the nonwoven fabric is melted to the basic structure. After the melt has solidified, a polymer structure having a non-oriented form is obtained from the nonwoven fabric, which is made of the same material as the nonwoven fibers. If the elasticity of the polymer is suited to allow deformations to the target diameter, an elastic element is obtained in the treated region of the membrane, which holds the particular section of the nonwoven fabric in a tensioned state due to the elastic residual stress. In this context, the target diameter shall be the desired diameter of the implant in the dilated state, wherein the target diameter is specified by the diameter of the vessel into which the implant is implanted. This effect can be used to counteract the formation of pockets of the nonwoven fabric in the blood stream, since the region having the elastic element builds higher radial tension than the untreated nonwoven fabric. In addition, the fiber ends of the nonwoven fabric are fixed in the region of the elastic element. When the elastic element extends around the entire circumference of the basic structure, the elastic element is also referred to as an elastic ring.

As an alternative, a section of the implant provided with the nonwoven fabric, preferably the distal or proximal end, can be pushed perpendicularly onto a substrate saturated with solvent or with a polymer solution, which preferably corresponds to the polymer of the nonwoven fabric. In this way, the parts of the nonwoven fabric that protrude in the particular section are dissolved and thereby cut to length, and also bound to the particular section of the basic structure. The film formation taking place as a result of the treatment with the solvent or polymer solution and the advantages, which in principle can be achieved thereby, correspond to the above explanations provided for the laser treatment for the production of the elastic element, since the film formation results in a non-oriented polymer accumulation, a fixation of fibers at the edges, and wetting of the basic structure. A fundamental difference between the laser treatment and the treatment with a solvent or a polymer solution is that the treatment with a solvent or a polymer solution effectively dissolves and removes material. This produces a considerably thinner, which is to say more filigree-like, material accumulation in the particular section of the implant, and therefore a thinner elastic element.

As an alternative, an elastic element can also be produced by way of a thermal treatment (such as by means of a heating element, inductive heating, IR radiation and/or light) at the particular section of the implant by fusing the fiber structure of the nonwoven fabric, and it can be fastened to the basic structure.

In other words, an elastic element can be produced from the nonwoven fabric by using an appropriate treatment of the implant in a region of the nonwoven fabric such that the nonwoven material melts down to the basic structure, accumulates there and solidifies, wherein the molten and subsequently solidified polymer has a certain level of elasticity. To this end, the elasticity must be sufficient, for example in the case of a stent graft, to permanently and without breakage allow the deformation of the treated structure to the crimped diameter (crimped state) and the radial expansion of the stent graft.

According to another embodiment of the method according to the invention, a hydrogel and/or a hydrogel-based adhesive can be disposed on the outside of the nonwoven fabric. The mechanism by which the development of flaps is prevented has been described above.

In a further embodiment, in the at least one section at least one torsion spring is inserted inside the implant and/or at least one torsion spring is placed on the outside, and/or preferably axially extending reinforcement elements are embedded into the nonwoven fabric in the at least one section. One embodiment for embedding the reinforcement elements into the nonwoven fabric has been described above.

It is also preferred when the nonwoven fabric is perforated in the at least one section by laser. This method has the advantage that higher porosity, such as for covering aneurysms, of the nonwoven fabric can be achieved, while maintaining the level of the compressive strength. Implants produced in this manner are used in particular in neurology.

The porosity or morphology of the nonwoven fabric can be controlled in a targeted fashion by suitably selecting the spinning parameters (such as the distance of the loaded nozzle to the basic structure (target), the spinning temperature, the air humidity, the solvent vapor concentration in the spinning apparatus, the high voltage difference between the nozzle and basic structure and/or the type of the solvent or solvent mixture). In addition, the porosity and morphology can be influenced by the concentration of the polymer solution and the throughput rate. By additionally applying heat radiation, a preferably axial orientation of the fiber(s) of the nonwoven fabric on the basic structure or the balloon can be achieved.

The method according to the invention and the implant according to the invention will be further described hereinafter in examples based on figures. All characteristics described and/or illustrated form the subject matter of the invention, regardless of their summarization in the claims or dependent claims.

DETAILED DESCRIPTION

Figure 1:
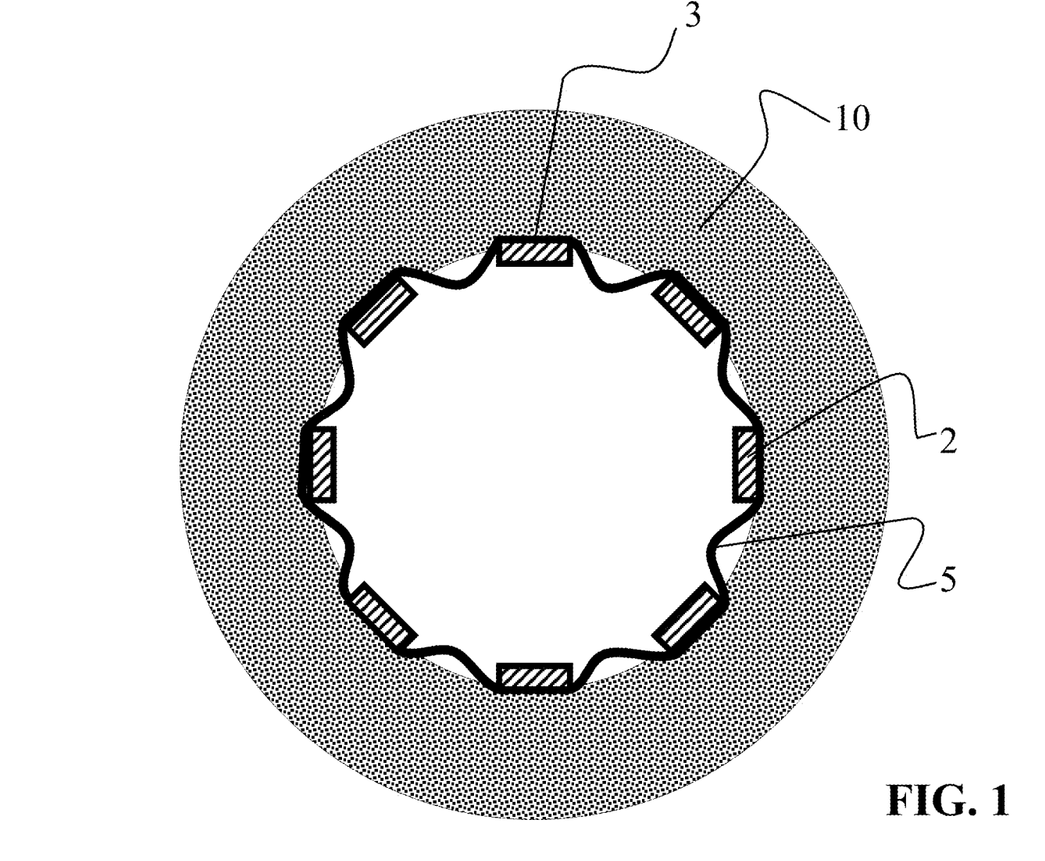
FIG. 1 is a cross-sectional illustration of a stent graft produced according to the prior art.

Turning to FIG. 1, a stent graft produced according to the prior art is shown in the dilated state, the graft being disposed inside a blood vessel 10. The nonwoven fabric 3 of the graft is disposed on the outer lateral surface of the basic structure, the struts 2 of which are visible in the illustration. It is easily apparent from FIG. 1 that the nonwoven fabric 3 forms flaps 5, which due to the pressure developing by the flow rate of the blood are pulled into the treated blood vessel 10, thereby preventing the flow of the blood.

Figures 2A, 2B:
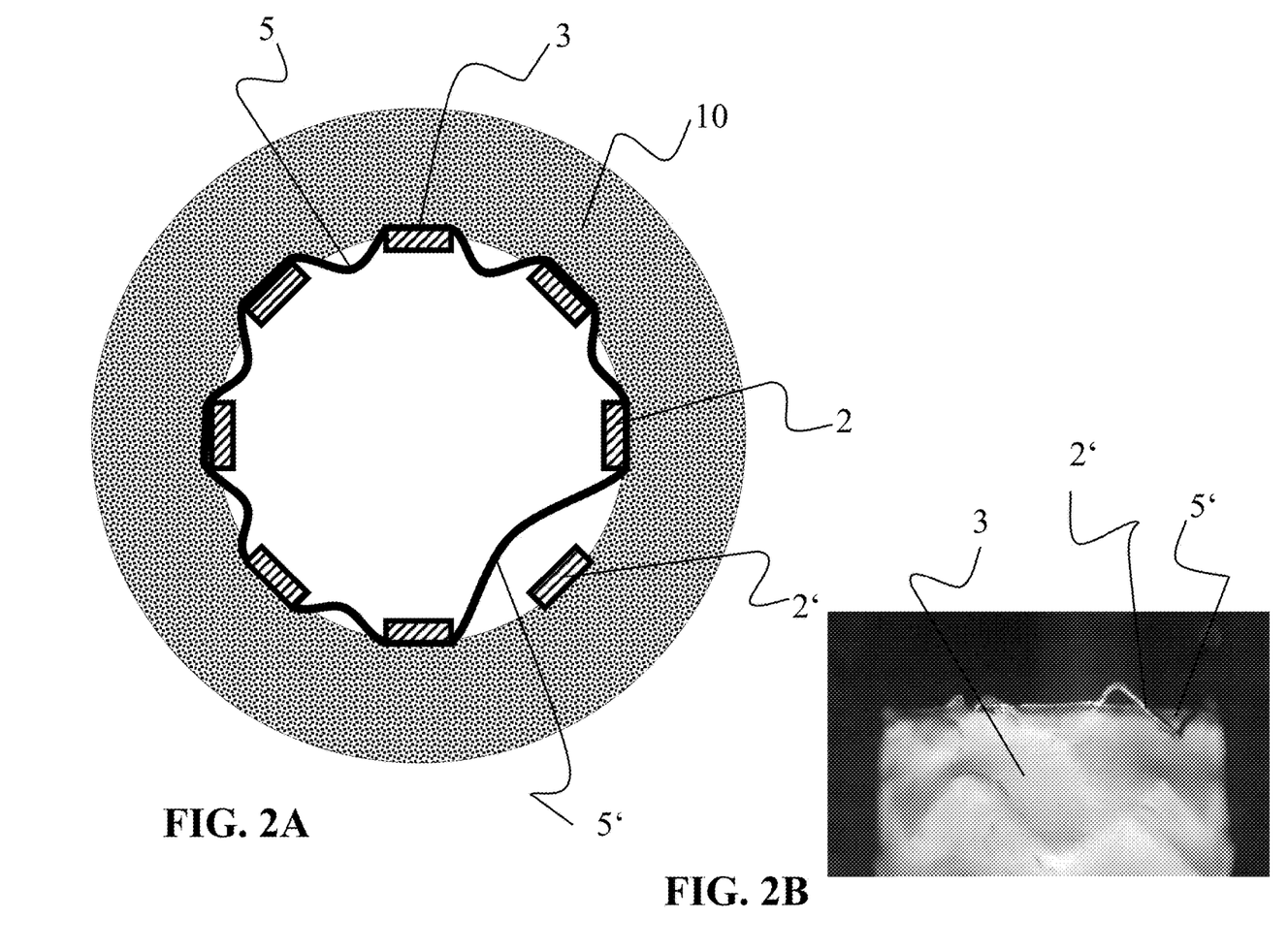
FIG. 2A is a cross-sectional illustration of a further stent graft produced according to the prior art and FIG. 2B is a photographic image thereof from the side.

It is apparent from FIGS. 2A-B that the flap formation in a stent graft produced according to the prior art can even extend over two mesh pieces of the basic structure. The flap 5' was created by the nonwoven fabric 3 detaching from the strut 2' and forms a very large pocket, which significantly impairs the blood flow in the blood vessel 10. The flap 5' is clearly visible in the photographic illustration in FIG. 2B.

Figure 3:
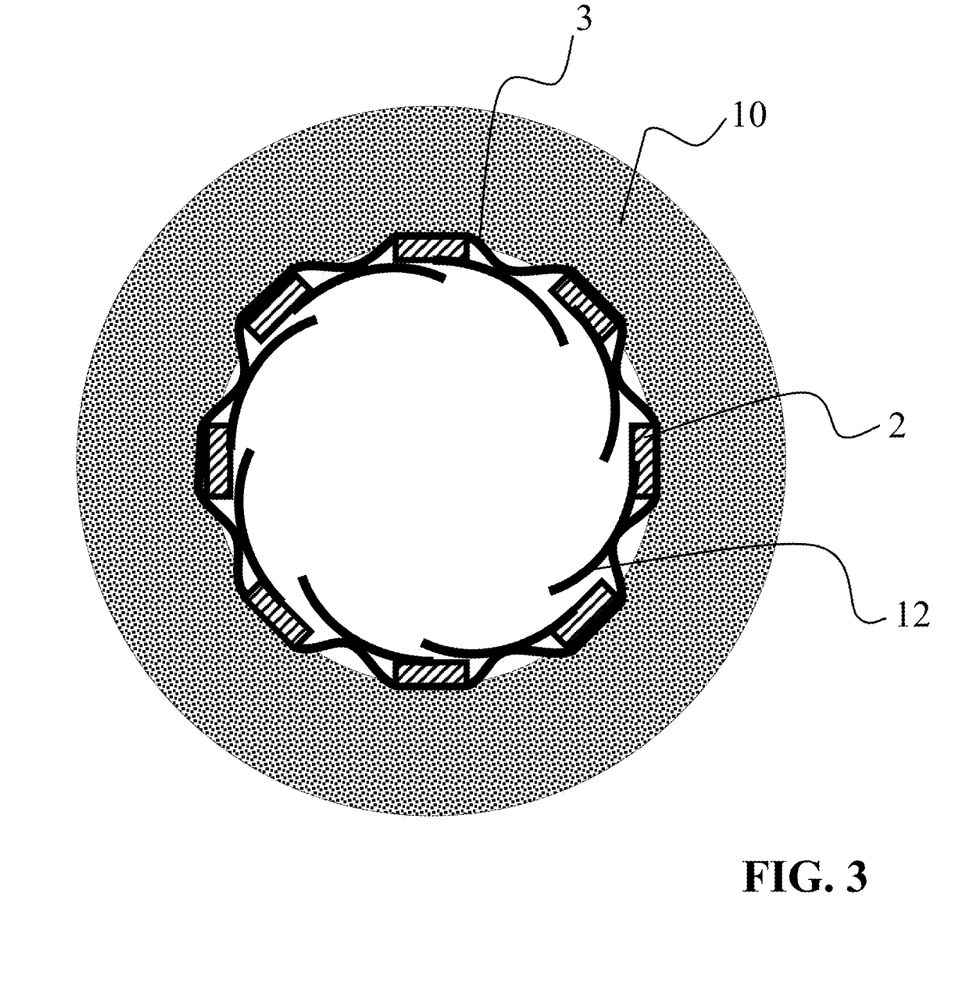
FIG. 3 is a cross-sectional illustration of a first embodiment of a stent graft according to the invention.

A first embodiment of a stent graft according to the invention shown in FIG. 3 comprises a torsion spring 12, which is disposed on the inner surface of the stent graft and which through the pressure acting from it outward ensures that no flaps can form or no extensive regions having fibers or fiber sections protrude into the interior of the vessel 10. In addition to the illustrated arrangement on the outer lateral surface of the basic structure, the nonwoven fabric 3 shown in FIG. 3 can also be disposed on the inside of the basic structure with the struts 2.

Figure 4:
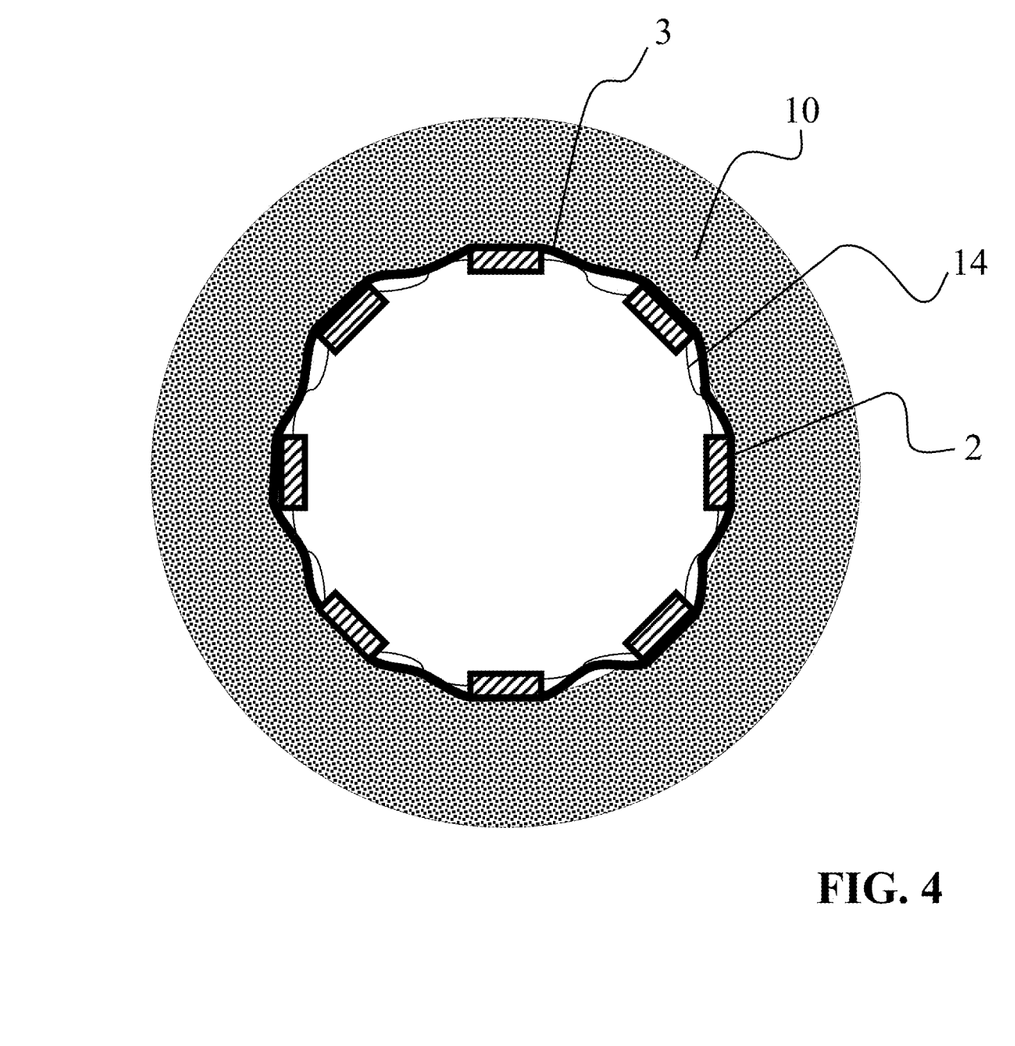
FIG. 4 is a cross-sectional illustration of a second embodiment of a stent graft according to the invention.

FIG. 4 shows a second embodiment of a stent graft according to the invention, wherein in this illustration too a nonwoven fabric 3 disposed on the inside of the basic structure with the struts 2 is not shown, but only the arrangement of the nonwoven fabric 3 on the outside. As an alternative, however, the nonwoven fabric 3 can also be arranged on the inside of the basic structure. The fastening means that the basic structure comprises are connectors 14 extending substantially in the circumferential direction and additionally connecting the struts to each other. Each connector 14 is made of the same material as the basic structure and have an S-shape.

Figures 5A, 5B:
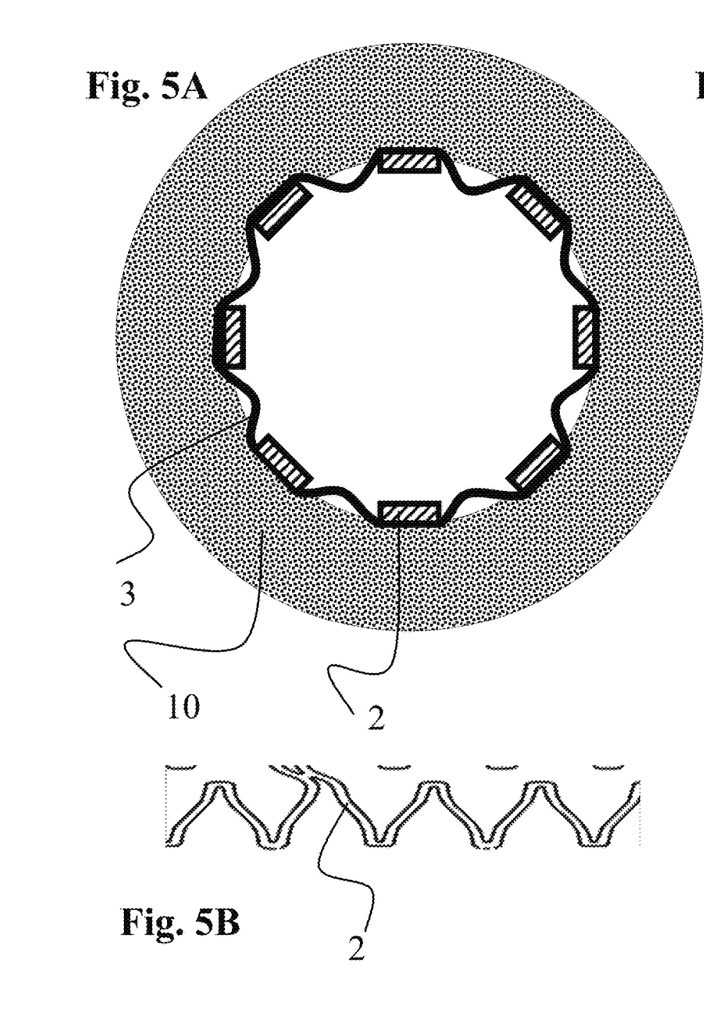
FIGS. 5A and 5B depict a cross-sectional illustration and a view of the base structure from the side, respectively, of a stent graft according to the prior art.
Figures 5C, 5D:
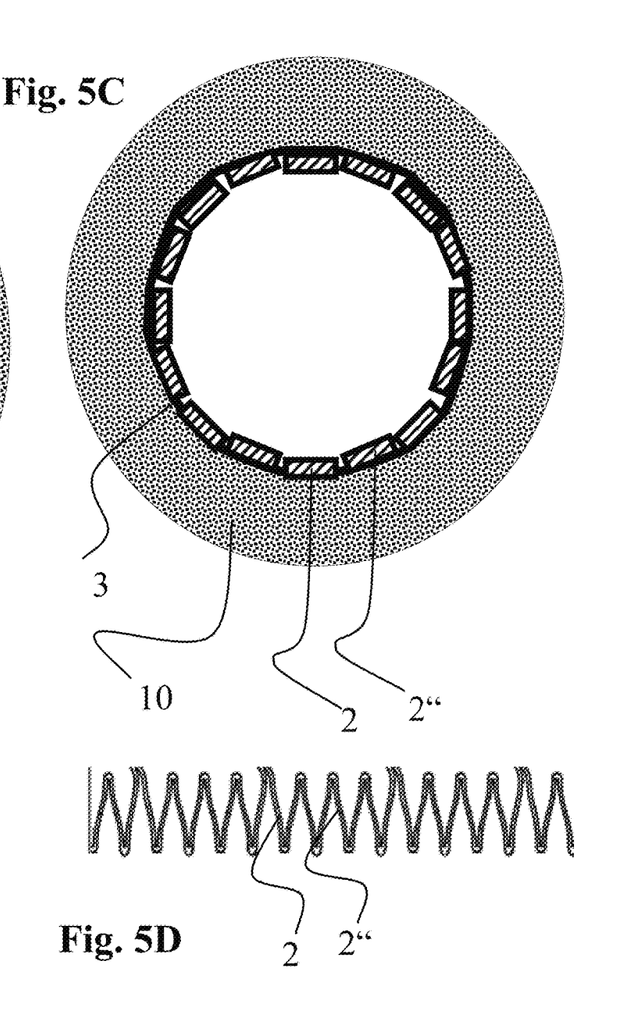
FIGS. 5C and 5D depict a cross-sectional illustration and a side view thereof, respectively, of a third embodiment of a stent graft according to the invention.

FIGS. 5C and 5D show a third embodiment of a stent graft according to the invention, which has a greater thickness on struts 2, 2" in one section. The greater thickness on struts 2, 2" is provided in those sections which are particularly susceptible to an increased risk of thrombosis, preferably at the proximal and/or distal ends of the implant. There, the nonwoven fabric is connected to the basic structure such that the nonwoven fabric, loose fibers or fiber sections cannot detach from the basic structure, in particular when feeding, positioning and releasing the implant and during the intended duration of function. In the remaining sections of the stent graft, the thickness of the struts 2 corresponds to the stent graft according to the prior art, which is shown for comparison in FIGS. 5A and 5B. Again, these illustrations do not show a nonwoven fabric that is disposed on the inside and/or the outside of the basic structure with the struts 2 or 2, 2".

Figures 6, 7:
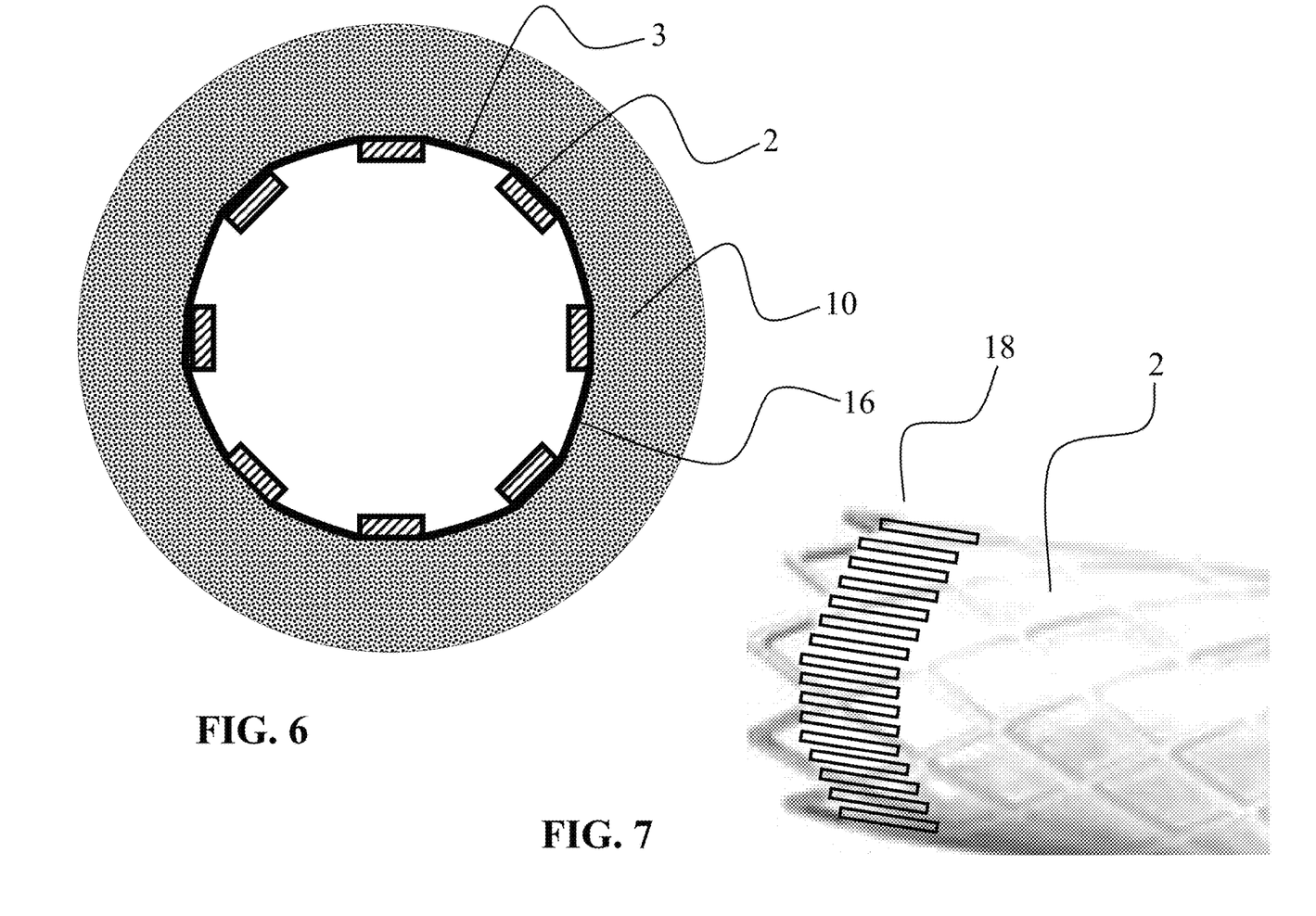
FIG. 6 is a cross-sectional illustration of a fourth embodiment of a stent graft according to the invention.
FIG. 7 is a side view of a fifth embodiment of a stent graft according to the invention.
Figure 8:
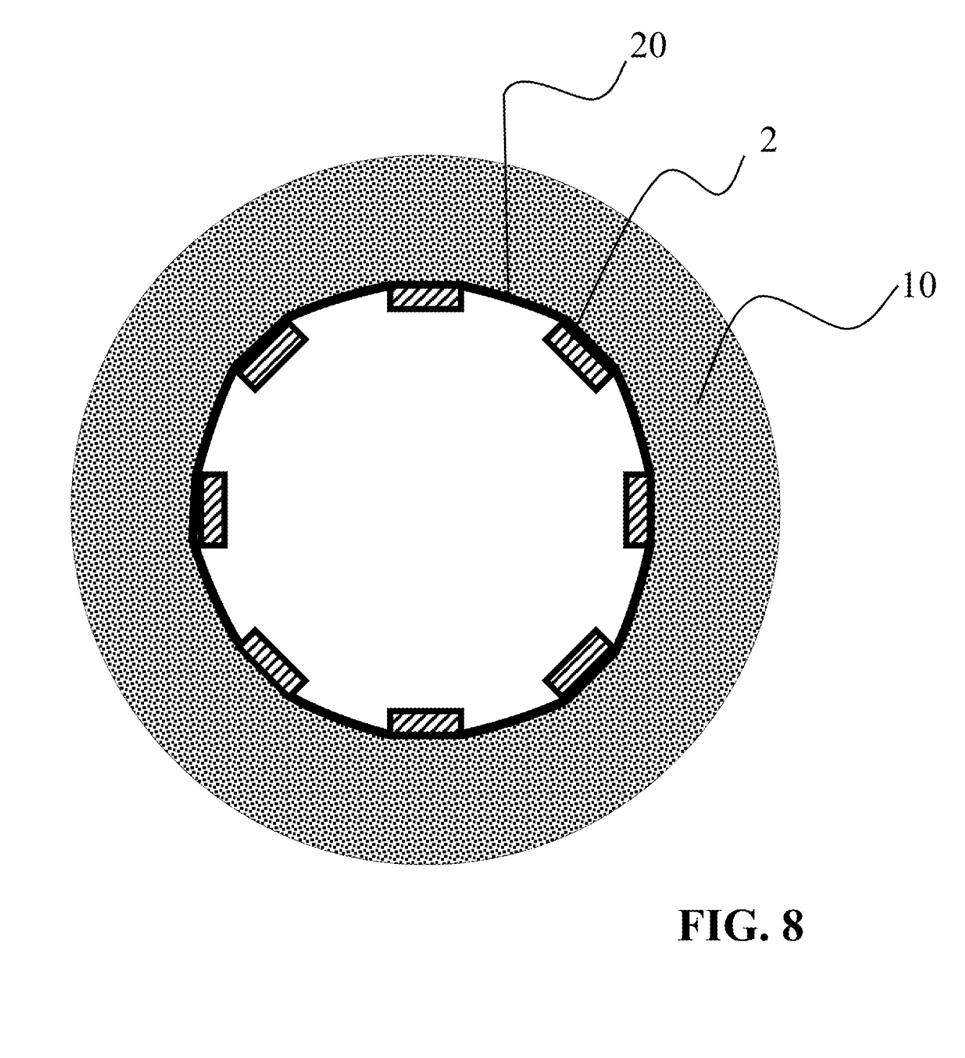
FIG. 8 is a cross-sectional illustration of a sixth embodiment of a stent graft according to the invention.
Figures 9A, 9B, 9C:
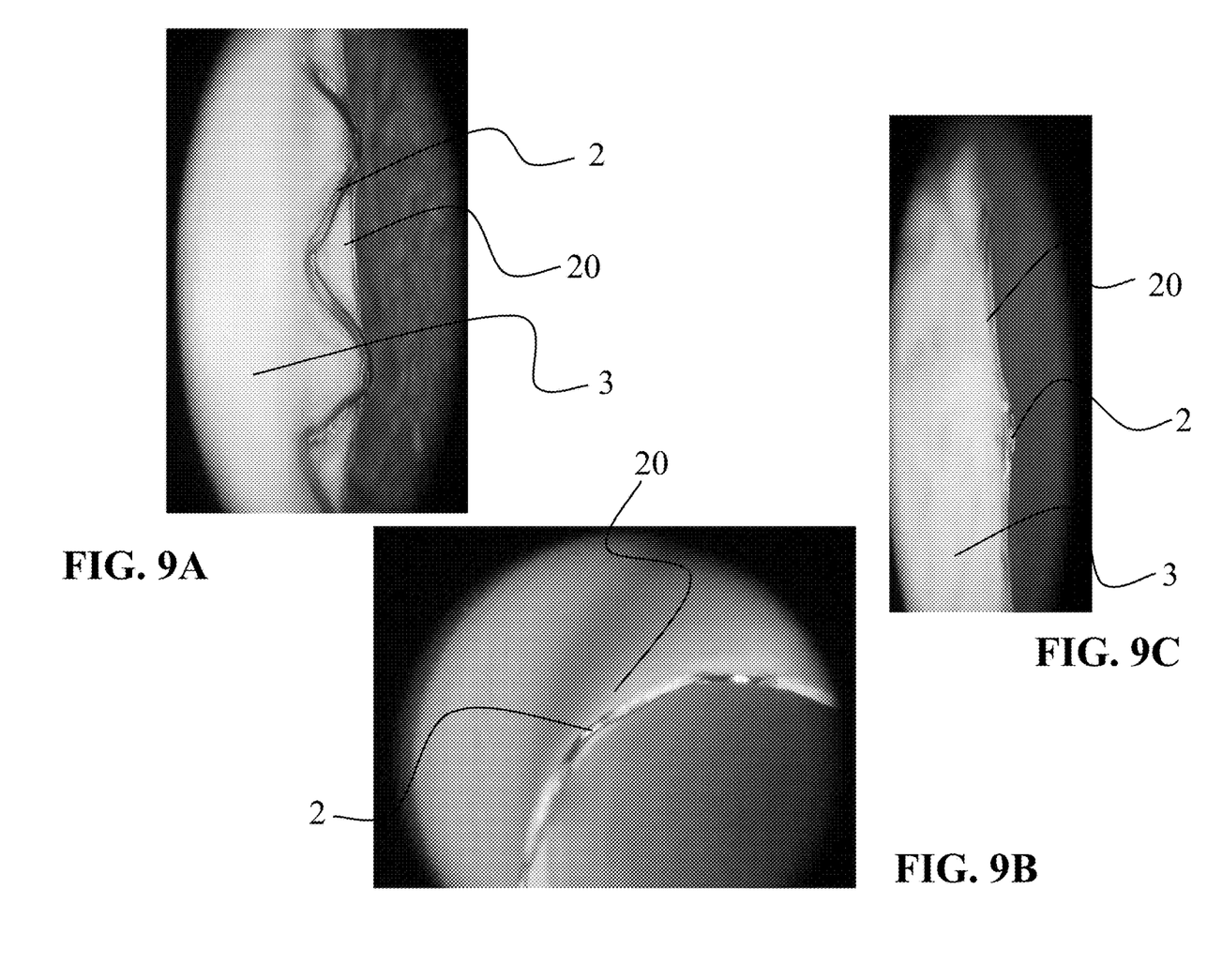
FIGS. 9A and 9C are two photographic images from the side and FIG. 9B is a photographic image from the front of the sixth embodiment shown in FIG. 8.

A fourth embodiment of a stent graft according to the invention shown in FIG. 6 illustrates the fastening means in the form of a coating 16, which is provided over the entire circumference of the stent graft and which is applied to the outside, the inside and/or the outside of the basic structure with the struts 2. The coating 16 comprises a material which forms a hydrogel and/or a hydrogel-based adhesive. The coating 16 with the hydrogel is swelled by water absorption from the blood of the blood vessel 10, so that an attractive interaction develops between the outer surface of the stent graft (that is, the outer surface of the nonwoven fabric) and the wall of the blood vessel 10. In this way, the stent graft is virtually glued to the blood vessel 10.

FIG. 7 shows a fifth embodiment of a stent graft according to the invention. In this embodiment, the fastening means is formed by axially extending reinforcement elements 18, which are provided on the basic structure with the struts 2 in the particular section. The advantage of these reinforcement elements 18 is that the nonwoven fabric is reinforced at the distal and proximal ends of the stent graft, thereby preventing flaps and lowering the risk of thrombosis. The reinforcement elements 18 are preferably embedded into the nonwoven material.

A last and sixth exemplary embodiment shown in FIGS. 8 and 9A-C has an elastic ring 20 preventing the formation of flaps at the distal and/or proximal ends of the stent graft. The elastic ring 20, as will be described in detail hereinafter, was formed by compaction from the material of the nonwoven fabric 3 shown in FIG. 8. This is clearly apparent in the photographs shown in FIGS. 9A-C.

EXAMPLES

A stent graft according to the invention is preferably produced by way of the methods described hereinafter.

First, a polymer solution is started from granules and dimethylformamide (DMF), wherein the polymer solution preferably comprises biocompatible thermoplastic polyurethane (TPU) in a concentration of 15% by weight to 25% by weight. The polymer solution is conducted in an apparatus having temperature and climate monitoring and/or control (temperature 20° C.-40° C., less then 30% relative humidity) by way of a syringe pump to a metal nozzle, to which a high voltage is applied. The throughput rate ranges between a minimum of 0.1 ml/h to a maximum of 10 ml/h. The basic lattice of the stent is pulled onto a conductive mandrel, which is grounded and rotates in front of the nozzle at a variable distance of 80 mm to 250 mm. Furthermore, an IR lamp is provided, which dries the filament pulled by the metal nozzle onto the basic lattice as a result of the applied high voltage. The dried filament forms the nonwoven fabric.

Thereafter, the stent with the nonwoven fabric can be compacted. The compacted stent is then cut and fixed by way of laser and/or solvent and/or thermal treatment. Afterwards, the stent graft can be crimped onto a stent delivery system (SDS). When using such a method, a stent graft is produced which comprises a compact nonwoven fabric, particularly on the outside thereof.

A stent graft having a TPU nonwoven fabric and produced according to the above method can be compacted in that the stent with the nonwoven fabric is pushed onto a PTFE tube and a layer of PTFE film is wrapped around the implant. Then, a heat-shrinkable tube is pulled over the PTFE film. The combination comprising the stent graft, PTFE tube and PTFE film with the heat-shrinkable tube is then pushed onto a metal pipe and inserted into a heater bar machine together with the metal pipe. Then, a temperature of 200° C. to 220° C. is produced in the machine for 8 seconds. Thereafter, the thermally treated stent graft is removed from the "packaging". The thermal treatment with the heat-shrinkable tube resulted in compacting of the nonwoven fabric, wherein the heat-shrinkable tube additionally produced a smooth and homogeneous nonwoven fabric lateral surface. Instead of a heater bar machine, it is also possible to use an inductive heat source.

Another interesting variant of the method is to mount the spun and optionally precompacted implant at the ends thereof on a tubular or solid mandrel after it has been cut to size (such as by rolling a blade of a stent graft disposed on a mandrel and spun there). Heater bars, which grab this mandrel at a distance of 0 to 2 mm from the end of the implant, allow the radiant heat and/or the heat dissipation of the mandrel to be used through an intensive heating pulse, which is limited in time, in order to bring about melting of the nonwoven fabric and the above-described production of an elastic element, in particular an elastic ring, in the edge region of the implant. Typical parameters for the method are, for example, placing the stent graft having an inside diameter of approximately 1.1 mm onto a stainless steel pipe having an outside diameter of 1.1 mm and an inside diameter of 0.95 mm. A heating pulse lasting 0.5 to 2 seconds by seizing the stainless steel pipe using the bars of a bar welder at a temperature of the heating bars of approximately 240° C. to approximately 300° C. (when using Pellethane, for example) and a length of the heating bars in the range of approximately 2 mm to approximately 5 mm, at a distance of approximately 0.2 mm from the distal or proximal end of the stent graft, results in very effective melting of the nonwoven fabric in the treated section and in the formation of the elastic element (see, for example, elastic ring 20 of the sixth embodiment of a stent graft according to the invention illustrated in FIGS. 8 and 9), wherein as a result of this treatment additionally fusing the nonwoven fabric to the basic structure of the implant is achieved, which initially continues along the longitudinal direction of the basic structure, but then steadily decreases. With this technique, the configuration of the composite of the basic body into a fiber structure is perceived to be particularly advantageous, because no localized connection in the edge region takes place, but instead a steadily increasing connection to the treated section of the implant. This may potentially have a favorable effect on the development of stress peaks in the composite of the basic body having the covering fiber structure, and enables a good combination of high deformation limits and secure fixation of the fiber structure to the basic structure of the implant.

As an alternative, compacting of the nonwoven fabric can be carried out by way of a $CO_2$ laser. Typical parameters for this are a relative output of the $CO_2$ laser of approximately 6-20 W, with a laser focus of approximately 1 $mm^2$, a rotation of the cylindrical spun implant of approximately 100-300 revolutions per minute, and an axial guiding speed of the implant of approximately 6 to 10 mm/second. The axial guiding speed shall be understood as the speed of the implant at which it is moved past the stationary laser source in the radial direction. The parameters listed described a practical operating point, in fact the parameters of radiation capacity and areal advancement can compensate for each other in order to provide the required melting energy. The process can be controlled very well technologically and can be used for superficial compaction, which preserves the porous fiber structure, or also comprehensive film formation for the production of an elastic element, or all stages between these two extremes.

Hereinafter, compacting of a PU nonwoven fabric by way of a solvent will be described. The conditioning of the electrospun nonwoven fabric over a period of less than two minutes in a saturated THF vapor phase at room temperature has proven to represent practical parameters for the method using THF-soluble polyurethanes. It was found that the parameters of the method additionally depend on the residual solvent content which may be present after the spinning process. By using solvent mixtures which reduce the vapor pressure of the swelling solvent, and by varying the temperature, the cross-linking homogeneity of the fiber structure of the nonwoven fabric can be influenced. The use of a mixture of THF and water (at a ratio of $THF/H_2O$ of 100%/0% to 30%/70% (each in % by volume), at room temperature) approximately doubles the selectable conditioning time of the nonwoven fabric, wherein due to diffusion effects the fiber structure can be swelled deeper and more homogeneously.

As an alternative to the nonwoven fabric formation described above, directly on the surface of the basic structure, it is possible to apply one or more fibers onto a grounded substrate surface (such as Tyvek film), which is placed at a defined distance in front of the nozzle. The electrospun nonwoven fabric is then wound onto a balloon. The balloon with the nonwoven fabric wound thereon is then placed in the inside lumen of a basic lattice of a stent. Thereafter, the balloon is expanded, thereby fixing the nonwoven fabric to the inside of the basic lattice. Then, the balloon is dilated in the vessel to be treated and pulled out of the stent graft. In principle, the method for avoiding protruding fibers, fiber sections or nonwoven fabric sections described above can also be applied to a stent graft having a nonwoven fabric on the inside thereof.

The two methods described above, which include the application of nonwoven fabric to the outside and/or inside, can also be combined.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implant formed as endovascular stent, the implant comprising:
   a basic structure formed as a hollow cylinder, wherein the basic structure comprises a magnesium alloy and/or biodegradable polymer;
   a nonwoven fabric disposed in and/or on the basic structure, the nonwoven fabric comprising a biocompatible thermoplastic polyurethane and/or a polymer selected from the group consisting of polylactic acid, polycaprolactone, a copolymer of polylactic acid and polycaprolactone, and a polyphosphazene;
   wherein at least one section of the implant further comprises a fastening means comprising a hydrogel or a hydrogel-based adhesive or the nonwoven fabric is treated to prevent or reduce, at least in an expanded state of the implant, either:
      a protrusion of nonwoven fabric sections from the basic structure, and/or
      formation of more extensive regions, which comprises fibers or fiber sections protruding from the basic structure.

2. The implant according to claim 1, characterized in that the fastening means is disposed on an outside of the nonwoven fabric.

3. The implant according to claim 1, characterized in that the fastening means comprises an elastic element, optionally an elastic ring.

4. The implant according to claim 1, characterized in that the nonwoven fabric is produced by way of electrospinning.

5. The implant according to claim 1, characterized in that treated nonwoven fabric comprises an increased thickness compared to pretreatment.

6. The implant according to claim 1, characterized in that, the hydrogel forms a bond with a pharmaceutically active substance or facilitates the embedding of such a substance.

7. The implant according to claim 6, characterized in that, the pharmaceutically active substance is heparin and/or heparansulfate.

8. The implant according to claim 1, characterized in that, the at least one section of the implant is at a proximal end of the implant.

9. The implant according to claim 1, characterized in that, the at least one section of the implant is at a distal end of the implant.

* * * * *